United States Patent [19]

Danielson et al.

[11] Patent Number: 5,155,166

[45] Date of Patent: Oct. 13, 1992

[54] USE OF 1-(1-PYRROLIDINYLCARBONYL)-PYRIDINIUM SALTS TO ATTACH COMPOUNDS TO CARBOXYLATED PARTICLES AND A KIT CONTAINING SAME

[75] Inventors: Susan J. Danielson; Donald P. Specht, both of Rochester, N.Y.

[73] Assignee: Eastman Kodak Company, Rochester, N.Y.

[21] Appl. No.: 539,680

[22] Filed: Jun. 18, 1990

[51] Int. Cl.$^5$ .................. C12Q 1/68; C07H 21/00; C07K 7/00; C12N 11/08

[52] U.S. Cl. .................. 525/54.1; 530/403; 530/404; 530/405; 530/408; 530/409; 530/812; 530/815; 530/816; 435/180; 435/181; 436/531; 436/532

[58] Field of Search ............ 525/54.1; 530/403, 404, 530/405, 408, 409, 812, 815, 816; 435/180, 181; 436/531, 532

[56] References Cited

U.S. PATENT DOCUMENTS

| | | | |
|---|---|---|---|
| 3,700,609 | 10/1972 | Tregear et al. | 525/426 |
| 4,181,636 | 1/1980 | Fischer | 525/54.1 |
| 4,199,363 | 4/1980 | Chen | 430/377 |
| 4,401,765 | 8/1983 | Craig et al. | 436/533 |
| 4,415,700 | 11/1983 | Batz et al. | 524/801 |
| 4,421,847 | 12/1983 | Jung et al. | 430/621 |
| 4,719,182 | 1/1988 | Burdick et al. | 436/533 |
| 4,859,736 | 8/1989 | Rink | 525/54.1 |
| 4,914,210 | 4/1990 | Levenson et al. | 548/413 |

FOREIGN PATENT DOCUMENTS 308235 3/1989 European Pat. Off. .

Primary Examiner—Nathan M. Nutter
Attorney, Agent, or Firm—James L. Tucker

[57] ABSTRACT

Useful materials for diagnostic tests, affinity chromatography, enzymatic reactions and immunoassays are prepared by covalently attaching reactive compounds containing reactive amino or sulfhydryl groups to polymeric particles having pendant carboxyl groups on the outer surfaces. Such reactive compounds include biologically reactive species, including enzymes, polypeptides and proteins. This attachment is carried out using specific carbamoylonium compounds, namely certain 1-(1-pyrrolidinylcarbonyl)pyridinium salts. These compounds react with the carboxyl groups on the particles to form intermediate reactive groups which then react with the amino or sulfhydryl groups to form a covalent linkage between particle and reactive compound. A kit comprises polymeric particles having carboxyl groups on the outer surfaces, and a 1-(1-pyrrolidinylcarbonyl)-pyridinium salt.

27 Claims, No Drawings

USE OF 1-(1-PYRROLIDINYLCARBONYL)PYRIDINIUM SALTS TO ATTACH COMPOUNDS TO CARBOXYLATED PARTICLES AND A KIT CONTAINING SAME

FIELD OF THE INVENTION

The present invention relates to a method for the preparation of polymeric particles having compounds attached thereto. In particular, it relates to the preparation of such materials by attachment of reactive amine- or sulfhydryl-containing compound to carboxylated polymeric particles using 1-(1-pyrrolidinylcarbonyl)-pyridinium salts. It also relates to a kit comprising polymeric particles and a 1-(1-pyrrolidinylcarbonyl)-pyridinium salt.

BACKGROUND OF THE INVENTION

Biologically active polypeptides or proteins which are attached to insoluble carrier materials, such as polymeric particles, have been used in a variety of ways. For example, the diagnosis of pathological or other conditions in human beings and animals is often carried out using immunological principles for the detection of an immunologically reactive species, for example antibodies or an antigen, in the body fluids of the person or animal. An antigen is generally known as a foreign substance, such as a drug, hapten, toxin, lectin, polypeptide or protein which, when introduced into the body, causes the production of certain soluble proteins known as antibodies.

Other proteins and amine-containing compounds, such as enzymes, avidin, biotin or polysaccarides, have been covalently linked to various carrier materials for use in affinity chromatography, enzymatic reactions, specific binding reactions and immunoassays. Among useful carrier materials are sheep and human erythrocytes, bacterial cells, latex particles, resinous particles and finely divided diazotized amino cellulose. For example, carrier particles prepared from sparingly water-soluble monomers (such as epoxy group-containing monomers) in the absence of emulsifiers are described in U.S. Pat. No. 4,415,700 (issued Nov. 15, 1983 to Batz et al). Other compounds, such as diamines, dihydrazides, mercaptoalkylamines and dimercaptans have been attached to carrier materials as linking moieties for later attachment of drugs, enzymes or other reactive species.

Carboxylated latex particles have also been used to prepare diagnostic reagents as described, for example, in U.S. Pat. No. 4,181,636 (issued Jan. 1, 1980 to Fischer). As described therein, the standard procedure for covalently attaching an immunologically reactive species to the particles having surface carboxyl groups involves the use of a water-soluble carbodiimide. While producing useful reagents, this procedure tends to activate the exposed reactive groups of the reactive species as well as the carboxyl groups. The result is intramolecular and intermolecular crosslinking or polymerization of the immunologically reactive species, and a significant portion of the species is thus impaired from complexation with a receptor molecule. Because the reactive species, for example an antibody, is usually very costly, this problem represents a serious economic loss. It has also been evident that the use of carbodiimides to attach proteins to carrier particles is not as efficient as desired at certain protein levels.

An important advance in the art was achieved with the use of carbamoylonium compounds which allows for rapid and more efficient attachment of biological compounds to carboxylated particles. The carbamoylonium compounds provide minimal crosslinking or deactivation of the reactive amino or sulfhydryl groups.

This advance is described in considerable detail in EP-A-O 308 235 (published Apr. 26, 1989, corresponding to U.S. Ser. No. 373,304, filed Jun. 29, 1989 by Sutton, Danielson, Bagchi and Scensny as a of U.S. Ser. No. 286,097, filed Dec. 19, 1988 which in turn is of U.S. Ser. No. 098,429, filed Sep. 18, 1987). The compounds are generically described in the noted reference. More particularly, pyridinium salts are described having piperidinylcarbonyl, piperazinylcarbonyl or morpholinylcarbonyl groups attached thereto. Named compounds are 1-(4-morpholinocarbonyl)-4-(2-sulfoethyl)-pyridinium hydroxide, inner salt, and 1-(4-morpholinocarbonyl)pyridinium chloride.

It has been found, however, that when the noted carbamoylonium compounds are used to attach proteins to carboxylated polymer particles, they generate strongly nucleophilic amine by-products (such as morpholine) in the course of the activation reactions. These by-products compete with the proteins for activated carboxylic sites on the particles, and tend to terminate attachment of proteins as sites are used up quickly. Thus, activation with the noted carbamoylonium compounds, such as 1-(4-morpholinocarbonyl)-4-(2-sulfoethyl)-pyridinium hydroxide, inner salt, is not very efficient.

It would be desirable to have more efficient activating agents which do not generate undesirable by-products.

SUMMARY OF THE INVENTION

An improvement in the art over the use of carbamoylonium compounds in general is provided with a method for attaching a reactive amine- or sulfhydryl-containing compound to polymeric particles comprising:

A. contacting (1) an aqueous suspension of carboxylated polymeric particles (2) a 1-(1-pyrrolidinylcarbonyl)pyridinium salt to produce reactive intermediate polymer particles having intermediate reactive groups, and B. contacting the reactive intermediate polymer particles produced in step A with a compound having a reactive amine or sulfhydryl group which reacts with the intermediate reactive groups to form a covalent linkage between the particles and the reactive compound.

Also provided by this invention is a kit comprising: a. polymeric particles having reactive carboxyl groups, or salts or precursors thereof, on the surface thereof, and (b) a 1-(1-pyrrolidinylcarbonyl)pyridinium salt.

The present invention provides a means for rapid and highly efficient attachment of reactive amine- or sulfhydryl-containing compounds to carboxylated polymeric particles. This attachment is achieved using a certain class of carbamoylonium compounds as the activating agents. The advantages generally accompanying the use of carbamoylonium compounds over other activating compounds are provided by the invention, but in addition, the activating agents used in this invention are more efficient as compared to other activating agents such as 1-(4-morpholinocarbonyl)-4-(2- sulfoethyl)-pyridinium hydroxide, inner salt. In particular, the specific class of activating agents used in this invention do not produce unwanted by-products which terminate activation. Thus, the activation reaction is much more efficient, requiring less time or compound to accomplish the desired attachment coverage. It has also been found that the activating agents used in the practice of this invention provide reagents having better retention of antibody activity as compared to the other activating agents.

These advantages are achieved, and shown below, by the use of a specific class of 1-(1-pyrrolidinylcarbonyl)-pyridinium salts as the activating agents. Such compounds have a weak nucleophilic leaving group, that is a pyrrolidinyl group, instead of a morpholino group, for example.

DETAILED DESCRIPTION OF THE INVENTION

The materials prepared according to the method of the present invention can be used in many different chemical and biological procedures. For example, they can be used in affinity chromatography, reactions catalyzed by enzymes, water purification, immunoassays wherein the analyte is an immunologically reactive species which has specific binding affinity for an attached polypeptide or protein, and other processes known to one of ordinary skill in the art. In some instances, the present invention can be used to attach intermediate linking moieties which can be further reacted with compounds of biological interest. Such compounds include, but are not limited to, amines, enzymes, amino acids, peptides, polypeptides, proteins, lipoproteins, glycoproteins, hormones, drugs, steroids, vitamins, polysaccharides, glycolipids, alkaloids, microorganisms, viruses, protozoa, fungi, parasites, rickettsia, molds, blood components, tissue and organ components, pharmaceuticals, haptens, lectins, toxins, nucleic acids, antigenic materials, biotin or derivatives thereof and components thereof.

The materials prepared by the present invention can be used for example in agglutination assays, particularly where the materials have a detectable tracer associated therewith. They can also be used in various solution and dry competitive assays, enzyme-linked immunosorbent assays, immunometric (or sandwich) assays and other assay formats where an insolubilized specific binding reagent is used. Dry assays are generally carried out using dry elements of some type. The details of such assay formats are not provided here because they are well known in the art. Specific details of useful assay formats and reagents are described in copending U.S. Ser. No. 539,774, filed on even date herewith by Sutton, Danielson, Findlay, Oakes, Oenick, Ponticello and Warren III (entitled "Biologically Active Reagents Prepared from Carboxy-Containing Polymer, Analytical Element and Methods of Use").

The method of this invention is a two-step process involving attaching a reactive amine- or sulfhydryl-containing compound which has a reactive amine or sulfhydryl group, respectively, to carboxylated polymeric particles using a specific carbamoylonium activating agent.

As used herein, the term "carboxylated particles" refers to particles having available surface reactive carboxyl groups, or salts thereof (for example, sodium, potassium and ammonium salts) or precursors thereof (such as anhydrides).

The polymeric particles useful in the method of this invention are generally water-insoluble particles having a particle size in the range of from about 0.01 to about 100 micrometers, and preferably from about 0.1 to about 3 micrometers. They can be homogeneous polymeric particles meaning that they are composed of the same polymer throughout, or they can be particles composed of more than one polymer such as graft copolymers as described, for example, in U.S. Pat. No. 3,700,609 (issued Oct. 24, 1972 to Tregear et al) and core-shell polymers described for example in U.S. Pat. No. 4,401,765 (issued Aug. 30, 1983 to Craig et al). It is critical that the polymeric particles have surface carboxyl groups available for attachment of the reactive amine- or sulfhydryl-containing compound. Such groups are preferably added to the particles by incorporating monomers containing such groups into the polymers (for example, acrylic acid, methacrylic acid, itaconic acid, and others described below). Alternatively, they can be added to the particles by further chemical reaction of a polymer having other precursor reactive groups which can be converted to carboxyl groups (for example, by hydrolysis of anhydrides, such as maleic anhydride, or by oxidation of surface methylol or aldehyde end groups).

Generally, useful polymeric particles can be prepared using any suitable polymerization technique, including emulsion (including batch, semi-continuous and continuous) and suspension polymerization techniques, graft copolymerization, and others known to one skilled in the polymer chemistry art. Emulsion polymerization is preferred as it can be used to provide generally smaller particles without the use of surfactants or emulsifiers as described for example in U.S. Pat. No. 4,415,700 (noted above) and *Research Disclosure* publication 15963 (July, 1977). *Research Disclosure* is a publication available from Kenneth Mason Publications, Ltd., The Old Harbourmaster's, 8 North Street, Emsworth, Hampshire PO10 7DD, England. Continuous emulsion polymerization is the most preferred technique, as described in the noted Research Disclosure publication.

Useful carboxylated particles are prepared from carboxylated styrene and its derivatives, carboxylated styrene-butadiene copolymers, acrylic and methacrylic acid polymers and other materials, many of which are commercially available.

Preferably, the carboxylated polymeric particles are composed of a polymer represented by the structure:

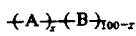

wherein A represents recurring units derived from one or more ethylenically unsaturated polymerizable monomers containing carboxyl groups or salts or precursors of such groups, and B represents recurring units derived from one or more ethylenically unsaturated polymerizable monomers.

Monomers from which A can be derived include, but are not limited to, acrylic and methacrylic acids, itaconic acid, aconitic acid, fumaric acid, maleic acid, $\beta$-carboxyethyl acrylate, $\beta$-carboxyethyl methacrylate, m and p-carboxymethylstyrene, methacrylamidohexanoic acid and N-(2-carboxy-1,1-dimethylethyl)acrylamide or a salt or anhydride precursor thereof.

Monomers from which B can be derived include, but are not limited to, styrene and styrene derivatives (for example vinyltoluene, 4-t-butylstyrene, divinylbenzene and 2-chloromethylstyrene), acrylic and methacrylic acid esters and amides (for example, methyl acrylate, ethyl methacylate, n-butyl acrylate, 2-ethylhexyl methacrylate, methyl methacrylate, 2-hydroxyethyl methacrylate, methacrylamide, ethylene dimethacrylate and 2-hydroxyethyl acrylate), sodium 2-acrylamido-2-methylpropanesulfonate, sodium 3-acryloyloxypropanesulfonate, p-styrenesulfonate, or acrylonitrile. Preferably, B is derived from styrene or a styrene derivative, or an acrylic or methacrylic acid ester.

For both the A and B monomers, it is important that the specific monomers used and their proportions be chosen so as to render the particles water-insoluble.

In the structure identified above, x is from about 0.1 to about 70, and preferably from about 1 to about 20, mole percent.

Particularly useful carboxyl-containing monomers from which A is derived are represented by the structure:

wherein R is hydrogen, halo or alkyl of 1 to 3 carbon atoms, M is hydrogen, an alkali metal ion or an ammonium ion and L is an organic linking group having from 8 to 50 atoms selected from the group consisting of carbon, nitrogen, oxygen and sulfur atoms in the linking chain.

Preferably, R is hydrogen or methyl, M is hydrogen or an alkali metal ion, and L comprises two or more alkylene or arylenealkylene groups which are connected or terminated with an oxy, thio, imino (—NR$^1$—), carbonyloxy (—COO—), carbonylimino (—CONR$^1$—), ureylene (—NR$^1$CONR$^1$—) or sulfonylimino (—SO$_2$NR$^1$—) group, wherein each R$^1$ is independently hydrogen, alkyl having 1 to 10 carbon atoms, cycloalkyl having 4 to 10 carbon atoms or aryl having 6 to 14 carbon atoms.

More particularly, L is p-phenylenemethyleneoxycarbonyltrimethylene, carbonyloxyethyleneoxycarbonyltrimethylene, carbonyloxyethyleneurylenepentamethylene, carbonylpenta(oxyethylene)oxycarbonyltrimethylene, carbonyldeca(oxyethylene)oxycarbonyltrimethylene, p-phenylenemethylenethioethyleneoxycarbonyltri-methylene, carbonyloxyethyleneiminocarbonyl-trimethylene, carbonyloxytetramethyleneoxycarbonyl-tetramethylene, p-phenylenemethyleneiminocarbonyl-trimethylene, p-phenylenemethyleneiminocarbonyltrimethylene, p-phenylene(methyl)iminoethyleneoxycarbonyltri-methylene, p-phenylenemethylenethioethylene, p-phenylenemethylenethioethyleneiminocarbonylmethyleneoxymethylene, p-phenylenemethylenethioethyleneimino-carbonylmethylenethiomethylene, p-phenylene-methylenethioethyleneiminocarbonyltrimethylene, phenylenemethylenethio-1-carboxyethylene, phenylenemethylenethiophenylene, phenylenemethylenethioethyleneoxyethylenethiomethyleneoxycarbonylethylene, phenylenemethyleneoxyphenylenemethylene-thioethylene, phenylenemethylenethioethyleneoxy-ethylenethioethyleneoxycarbonylethylene, phenylene-methyleneoxyphenylenemethylenethiophenylenemethylene-thiotrimethylene and phenylenemethylenethioethylene-oxyethylenethioethyleneoxycarbonylphenylene.

Representative monomers from which A is derived are selected from the group consisting of: mono-m and p-vinylbenzyl glutarate, mono-p-vinylbenzyl glutarate, mono-2-methacryloyloxyethyl glutarate, 2-(4-carboxybutyramido)ethyl methacrylate, 2-[N'-(5-carboxypentyl)ureido]ethyl methacrylate, mono-methacryloylpenta(oxyethylene) glutarate, mono-(4-acryloyloxybutyl) glutarate, 4-(4-carboxybutyramido)styrene, mono-methacryloyldeca(oxyethylene) glutarate, mono-2-(p-vinylbenzylthio)ethyl glutarate, mono-2-(m and p-vinylbenzylthio)ethyl glutarate, 4-(4-carboxybutyramidomethyl)styrene, mono-2-[N-methyl-N-(4-vinylbenzyl)amino]ethyl glutarate, 3-(p-vinylbenzylthio)propionic acid, 4-[2-(4-carboxybutyramido)ethylthiomethyl]styrene, 4-[2-(carboxymethoxyacetamido)ethylthiomethyl]styrene, 4-[2-(carboxymethylthioacetamido)ethylthiomethyl]styrene, mono-2-(4-vinylbenzylthio)ethyl succinate, 4-[2-(carboxymethoxyacetoxy)ethylthiomethyl]styrene, mono-4-vinylbenzyl succinate, 2-(4-vinylbenzylthio)succinic acid, 2-(4-vinylbenzylthio)benzoic acid, mono-2-[2-(4-vinylbenzylthio)ethoxy]ethylthiomethyl malonate, mono-methacryloylpenta(oxyethylene) phthlate, mono-methacryloyldeca(oxyethylene) phthalate, mono-2-{2-[2-(4-vinylbenzylthio)ethoxy]ethylthio}ethyl succinate, mono-2-{2-[2-(4-vinylbenzylthio)ethoxy]ethylthio}ethyl phthalate, 3-[4-(4-vinylbenzyloxy)benzylthio]propionic acid and 4-{4-[4-(4-vinylbenzyloxy)benzylthio]benzylthio}butyric acid. The monomer 3-(p-vinylbenzylthio)propionic acid is one of the more preferred monomers.

Representative polymers of which the polymeric particles are composed include poly(styrene-co-vinylbenzyl chloride-co-acrylic acid) (85:10:5 molar ratio), poly(styrene-co-acrylic acid) (99:1 molar ratio), poly(styrene-co-methacrylic acid) (90:10 molar ratio), poly(styrene-co-acrylic acid-co-m and p-divinylbenzene) (89:10:1 molar ratio), poly(styrene-co-2-carboxyethyl acrylate) (90:10 molar ratio), poly(methyl methacrylate-co-acrylic acid) (70:30 molar ratio), poly(styrene-co-butyl acrylate-co-methacrylic acid) (45:45:10 weight ratio), poly(styrene-co-mono-2-methacryloyloxyethyl glutarate) (97.84:2.16 molar ratio), poly[styrene-co-monomethacryloylpenta(oxyethylene) glutarate] (98.7:1.3 molar ratio), poly[styrene-co-monomethacryloyldeca(oxyethylene) glutarate] (99.2:0.8 molar ratio), poly[styrene-co-mono-2-(m and p-vinylbenzylthio)ethyl glutarate] (98.3:1.7 molar ratio), poly[styrene-co-2-(4-vinylbenzylthio)succinic acid] (97.98:2.02 molar ratio), poly[styrene-co-2-(4-vinylbenzylthio)benzoic acid] (97.75:2.25 molar ratio), poly{{styrene-co-mono-2-{2-[2-(4-vinylbenzylthio)ethoxy]ethylthio}ethyl succinate}} (98.64:1.36 molar ratio), poly{{styrene-co-mono-2-{2-[2-(4-vinylbenzylthio)ethoxy]ethylthio}ethyl phthalate}} (98.79:1.21 molar ratio), poly(styrene-co-mono-m and p-vinylbenzyl glutarate) (97.84:2.16 molar ratio), poly[styrene-co-mono-2-(p-vinylbenzylthio)ethyl glutarate] (98.25:1.75 molar ratio), poly[styrene-co-3-(p-vinylbenzylthio)propionic acid] (97.59:2.41 molar ratio), poly[styrene-co-mono-2-(4-vinylbenzylthio)ethyl succinate] (98.17:1.83 molar ratio), poly{styrene-co-4-[2-(carboxymethoxyacetoxy)ethylthiomethyl]styrene} (98.26:1.74 molar ratio), poly(styrene-co-mono-4-vinylbenzyl succinate) (97.71:2.29 molar ratio), poly[styrene-co-mono-methacryloylpenta(oxyethylene) phthalate] (98.81:1.19 molar ratio), poly[styrene-co-mono-methacryloyldeca(oxyethylene) phthalate] (99.19:0.81 molar ratio), poly[styrene-co-3-p-(vinylbenzylthio)propionic acid] (95.2:4.8), poly(methyl methacrylate-co-mono-m and p-vinylbenzyl glutarate) (88.8:11.2 molar ratio), poly(butyl acrylate-co-mono-2-methacryloyloxyethyl glutarate) (90.9:9.1 molar ratio), poly[butyl methacrylate-co-mono-(4-acryloyloxybutyl glutarate] (79.3:20.7 molar ratio), poly[styrene-co-3-(p-vinylbenzylthio)propionic acid-co-2-hydroxyethyl acrylate] (92.6:2.4:5 molar ratio), and poly[styrene-co-mono-methacryloyldeca(oxyethylene) phthalate-co-mono-deca(oxyethylene) methacrylate] (93:1:6 molar ratio).

Further details regarding preferred carboxylated polymers are provided in copending U.S. Ser. No. 539,768 filed on even date herewith by Ponticello and Sutton and entitled "Carboxy Containing Monomers and Polymers and Latices Prepared from Same", now abandoned in favor of copending U.S. Ser. No. 654,112 of Ponticello et al, filed Feb. 12, 1991.

In one embodiment, the particles are core-shell particles wherein the core is composed of a first polymer, and the shell is composed of a carboxylated second polymer as described above. If desired, a dye can be incorporated within the core to provide a detectable tracer for agglutination assays.

The carboxylated polymeric particles described herein can be supplied as a dried powder which can be resuspended for any use of interest. Preferably, however, they are supplied as an aqueous suspension generally having from about 0.1 to about 35 percent solids. Suspending agents, buffers or other addenda can be included in the suspension if desired.

A specific class of carbamoylonium compounds are used for covalent attachment of the reactive amine- or sulfhydryl-containing compound to the carboxylated polymeric particles in the practice of this invention. These compounds are 1-(1-pyrrolidinylcarbonyl)-pyridinium salts which have a substituted or unsubstituted pyrrolidinyl ring connected to a substituted or unsubstituted pyridinium ring through a carbonyl group on the cation, and a suitable anion to form the salt. More specifically, the salts can be represented by the structure:

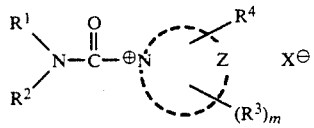

wherein Z represents the carbon atoms necessary to complete a pyridinium ring, and m is 0 or 1.

Also in this structure, $R^1$ and $R^2$ together represent the carbon atoms necessary to complete, with the nitrogen atom to which they are attached, a substituted or unsubstituted pyrrolidinyl ring. The pyrrolidinyl ring can be substituted with one or more alkyl groups having 1 to 8 carbon atoms (methyl, ethyl, isopropyl and chloromethyl) or one or more halo groups (such as chloro, bromo or iodo). Preferably, the pyrrolidinyl ring is unsubstituted or substituted with alkyl having 1 to 3 carbon atoms or halo (for example, chloro).

$R^3$ is substituted or unsubstituted alkyl having 1 to 8 carbon atoms (such as methyl, ethyl, isopropyl, t-butyl, benzyl, chloromethyl), cycloalkyl having 5 to 10 carbon atoms (such as cyclopentyl and cyclohexyl), aryl having 6 to 10 carbon atoms (such as phenyl, naphthyl, xylyl and tolyl), or a 5- to 7-membered heterocyclic group having one or more nitrogen, sulfur or oxygen atoms with the necessary carbon atoms to complete the ring (such as pyridinyl, pyrrolidinyl, morpholino and piperazinyl).

In addition, $R^3$ and $R^4$, taken together, can represent the carbon atoms necessary to complete, with the pyridinium ring, a fused 5- to 7-membered carbocyclic or heterocyclic ring. Thus, in this embodiment, representative fused ring moieties include, but are not limited to, benzo and naphtho.

$R^4$ can also be hydrogen, substituted or unsubstituted alkyl having 1 to 8 carbon atoms (such as methyl, ethyl, isopropyl, t-butyl, hexyl, benzyl, chloromethyl, sulfonate and ethylenesulfonate). Where m is 0, $R^4$ can also be any of:

(a) —$NR^5CO$—$R^6$ wherein $R^5$ is hydrogen or substituted or unsubstituted alkyl having 1 to 6 carbon atoms (such as methyl, ethyl, isopropyl, pentyl and hexyl), and $R^6$ is hydrogen, substituted or unsubstituted alkyl as defined for $R^5$, or —$NR^7R^8$ wherein $R^7$ and $R^8$ are independently hydrogen or substituted or unsubstituted alkyl as defined for $R^5$, (b) —$(CH_2)_n$—$NR^9R^{10}$ wherein $R^9$ is —$COR^{11}$, $R^{10}$ is hydrogen or substituted or unsubstituted alkyl as defined for $R^5$, $R^{11}$ is hydrogen or substituted or unsubstituted alkyl as defined for $R^5$ or —$NR^{12}R^{13}$ wherein $R^{12}$ is substituted or unsubstituted alkyl as defined for $R^5$ or substituted or unsubstituted aryl having 6 to 10 carbon atoms (such as phenyl, xylyl, naphthyl and tolyl), and $R^{13}$ is hydrogen, substituted or unsubstituted alkyl or substituted or unsubstituted aryl as defined for $R^{12}$, and n is 1 to 3, and (c) —$(CH_2)_q$—$CONR^{14}R^{15}$ wherein $R^{14}$ is hydrogen, substituted or unsubstituted alkyl or substituted or unsubstituted aryl as defined for $R^{12}$, $R^{15}$ is hydrogen or substituted or unsubstituted alkyl as defined for $R^5$, or $R^{14}$ and $R^{15}$ together represent the atoms necessary to complete a 5- to 7-membered aliphatic ring, and q is 0 to 3.

In preferred embodiments, m is 0 and $R^4$ is hydrogen, substituted or unsubstituted alkyl, substituted or unsubstituted aryl, pyridinyl, or when m is 1, $R^3$ and $R^4$ together represent the carbon atoms necessary to complete a 6-membered fused carbocyclic ring.

In the noted structure above, $X^-$ represents an anion or an anionic portion of the compound to form an intramolecular salt. Representative anions include, but are not limited to, halide (such as chloride, bromide or fluoride), tetrafluoroborate, nitrate, sulfate, p-toluenesulfonate, perchlorate, methosulfate, hydroxide and hexafluorophosphate. $X^-$ can also be a sulfonate or an alkylenesulfonate attached to the pyridinium ring, the alkylene portion having from 1 to 6 carbon atoms. The chloride salt is preferred.

Representative activating agents useful in the practice of this invention are listed as follows, with the understanding that many others not listed would be readily apparent to one skilled in the art:

COMPOUNDS

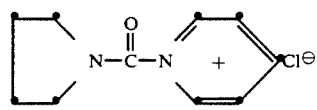

I.

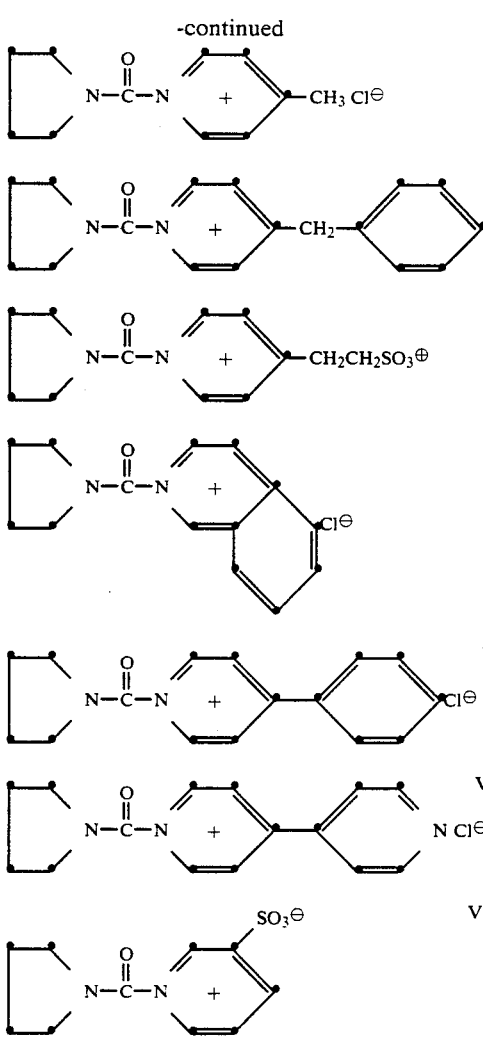

Compound I, which is 1-(1-pyrrolidinylcarbonyl)-pyridinium chloride, is preferred.

The carbamoylonium compounds useful in the practice of this invention can be obtained commercially, or prepared using known procedures and starting materials, as described in U.S. Pat. No. 4,421,847 (issued Dec. 20, 1983 to Jung et al) and references noted therein.

Any reactive amine- or sulfhydryl-containing compound can be attached to carboxylated polymeric particles according to the present invention as long as that compound contains a reactive amine or sulfhydryl group, respectively, which will react with the intermediate formed by the reaction of the carbamoylonium compound with carboxyl groups on the particles. In certain embodiments, the reactive amine- or sulfhydryl-containing compound is a polypeptide or protein which is biologically active. The term "biologically active" refers to its capacity for interaction with another component which may be found in physiological fluids. Such an interaction can be catalytic activity in the case where the material is an enzyme. In addition, the interaction can be a complexation which occurs between materials which have affinity for one another, such as avidin with biotin or antibodies with antigens, and the like. In other embodiments, the reactive amine- or sulfhydryl-containing compound is a diamine, polysaccharide, amino acid, peptide or protein which can be a linking moiety for attaching a second compound to the particle. Such second compounds include, but are not limited to, enzymes, antibodies, antigens, drugs, biotin or derivatives thereof and others readily apparent to one skilled in the art.

Preferably, the reactive amine- or sulfhydryl-containing compound is an immunologically reactive species, including but not limited to the biological and chemical compounds listed above. More preferably, it is an antibody, such as an antibody directed against a drug, hormone, Streptococcus A antigen, a chlamydial antigen, a gonococcal antigen, human chorionic gonadotropin, human leutinizing hormone or a herpes virus. Alternatively, the immunologically reactive species can be an antigen, such as an antigen of HTLV-I or HIV-I.

In still other embodiments, the reactive compound can be a nucleic acid or derivative thereof which has been modified to have the requisite reactive amine or sulfhydryl groups for attachment to carboxylated particles. Procedures for modifying nucleic acids are well known as described, for example, in U.S. Pat. No. 4,914,210 (issued Apr. 3, 1990 to Levenson et al) and WO-A-89/2932 (published Apr. 6, 1989), both directed to modification of oligonucleotides, U.S. Pat. No. 4,719,182 (issued Jan. 12, 1988 to Burdick et al), Erlander et al, *J. Biol. Chem.*, 234, 1090 (1959), Wiston et al, *Biochim. Biophys. Acta*, 612, pp. 40–49 (1980) and Borzini et al, *J. Immunol. Methods*, 44, pp. 323–332 (1981).

In certain embodiments, the materials prepared by the method of this invention can have a tracer associated therewith. A tracer is a detectable species which enables one to detect the reagent. Useful tracers include radioisotopes, colorimetric or fluorometric compounds, enzymes, chemiluminescent compounds, phosphorescent compounds and others known to one skilled in the art. Particularly useful tracers are colorimetric and fluorometric compounds. The tracer can be associated with the reagent in any suitable manner. For example, the tracer can be associated (for example, covalently or ionically attached) with the biologically active polypeptide or protein. Alternatively and preferably, the tracer is associated with the polymeric particles, for example attached (covalently or adsorbed) to their outer surface or internally distributed in part or all of the volume, or both.

It is particularly desirable to incorporate tracers such as colorimetric or fluorometric dyes into the particles. Such incorporation can be accomplished by polymerizing monomers having dye or dye precursor moieties attached to the polymerizable vinyl group. Preferably, however, the dyes are "loaded" into the particles after their formation using known procedures noted below.

Particularly useful tracers which can be incorporated into particles include cyan, yellow and magenta dyes, fluorescent europium and other rare earth chelates (such as a mixture of europium-thenoyl trifluoroacetonate and trioctylphosphine oxide), fluorescent dyes such as 2,5-bis(6-butyl-2-benzoxazolyl)thiophene and 3-(2-benzothiazolyl)-7-diethylaminocoumarin and others known in the art. Incorporation of dyes can be achieved using the techniques described in U.S. Pat. No. 4,199,363 (issued Apr. 22, 1980 to Chen) and in copending U.S. Ser. No. 136,214 (filed Dec. 18, 1987 by Sutton).

The method of the present invention is carried out in two steps, the first of which involves contacting an aqueous suspension of the polymeric particles described above with a carbamoylonium compound described above to produce reactive intermediate polymer particles having intermediate reactive groups in place of the carboxyl groups. This step is carried out at a suitable pH using suitable acids or buffers to provide the desired pH. Generally, the pH is less than 6, but this is not critical as long as the reaction can proceed. More likely, the pH is between about 3.5 and about 6. The molar ratio of carbamoylonium compound to the total measured carboxylic acid level in the polymer particles is from about 1:1 to about 200:1, and preferably from about 2:1 to about 100:1.

In the second step of the method, the reactive intermediate formed in the first step is contacted with a reactive amine- or sulfhydryl-containing compound having a reactive amine or sulfhydryl group, respectively, which will react with the intermediate reactive group of the reactive intermediate. A covalent linkage is thereby formed between the particles and the reactive compound. The weight ratio of the reactive compound to the polymeric particles is generally from about 1:2000 to about 1:2, and preferably from about 1:200 to about 1:10.

This second step can be carried out at a suitable pH such that the desired reaction occurs without premature agglutination. The pH may be varied depending upon the reactants involved and their concentration in the reaction medium. For many proteins and polypeptides, this pH will be greater than 6.

The method of the invention is generally carried out at a temperature of from about 10° to about 60° C., and preferably from about 15 to about 30° C. The temperature can be the same or different for the two steps of the method.

When certain activating agents are used with certain reactive compounds, it may be desirable to remove excess activating agent. Removal may be generally carried out by centrifuging or filtering the particles, accompanied by suitable washings and resuspensions in suitable buffers.

Further details regarding the method of this invention would be readily apparent to one of ordinary skill in the art from the representative examples described below.

The polymeric particles described above can be provided in a kit which also includes one or more of the carbamoylonium compounds as described herein. The particles can be free of tracer, or have a tracer associated therewith. Useful tracers are noted above, but preferred tracers include colorimetric and fluorometric dyes which have been incorporated into the particles in a suitable manner. The particles can be supplied as a powder as long as it can be resuspended for any use of interest. Preferably, they are supplied as an aqueous suspension as described above.

Such kits can optionally include a compound having reactive amine or sulfhydryl groups for attachment to the polymeric particles in the method of this invention. Other optional materials include pipettes, test tubes, instructions, buffers or other reagents and equipment which may be helpful in the practice of the invention.

The following examples are provided to illustrate the practice of the method of this invention and to demonstrate the improvements obtained thereby. All percentages are by weight unless otherwise noted.

EXAMPLE 1

Preparation of Thyroxine Reagents

This example illustrates the practice of this invention to attach various antibodies directed to thyroxine to carboxylated polymeric particles to provide reagents for thyroxine immunoassays. It also compares the reagents so prepared to similar reagents prepared without carboxylated particles.

Materials:

The activating agent used was 1-(1-pyrrolidinylcarbonyl)pyridinium chloride prepared by procedures generally described in GB-A-1,383,630, that is, the reaction of 1-pyrrolidinylcarbonyl chloride with pyridine.

The carboxylated particles were composed of poly[styrene-co-mono-2-(p-vinylbenzylthio)ethyl glutarate] (98.25:1.75 molar ratio), prepared using the procedures described in U.S. Ser. No. 539,768 (Ponticello and Sutton, noted above).

Control polymeric particles were composed of poly[styrene-co-m and p-(2-chloroethylsulfonylmethyl)styrene (60:40)-co-ethylene dimethacrylate] (94.5:4.5:1 molar ratio), prepared using the procedures described in U.S. Ser. No. 081,206 (filed Aug. 3, 1987 by Sutton and Danielson).

The antibodies directed to thyroxine were obtained as follows:

| | |
|---|---|
| A | O.E.M. Concepts, Inc. (clone 02-1007-115) |
| B | Cambridge/Ventrex (lot A4641) |
| C | Cambridge/Ventrex (lot A7641) |
| D | Biodesign (clone 208) |
| E | BiosPacific (clone 036 A2207B) |
| F | BiosPacific (clone 035-2206A) |
| G | Beckman (lot 906071) |
| H | BiosPacific (clone 035 A2205B) |
| I | Beckman (lot 906131) |
| J | Hyclone (lot RD664) |
| K | O.E.M. Concepts, Inc. (clone 02-911-112) |

Method:

The anti-thyroxine antibodies were attached to the carboxylated polymeric particles in the following manner. The final dispersion comprised 1% of antibodies per gram of particles (0.3 mg of antibodies per 30 mg of dry polymer weight) in 2-(4-morpholinoethanesulfonic acid buffer (0.1 molar, pH 5.5).

The dispersion was prepared by adding a suspension of particles (30 mg) in a large microfuge tube, and bringing the volume to 1.5 ml with buffer. The suspension was centrifuged for 15 minutes at 14,000 rpm, and the supernatant discarded. Buffer (1 ml, 0.1 molar) was added to the tube, followed by addition of activating agent solution (300 μl). This solution had been prepared by dissolving the agent (160 mg) in buffer (0.1 molar, 5 ml).

The tube was capped and rotated end-over-end at room temperature for 10 minutes. A solution of the antibodies (0.3 mg protein) was added to each tube followed by end-over-end rotation for 24 hours at room temperature.

Reaction of antibodies with the activated carboxyl groups on the particles was quenched by addition of bovine serum albumin (250 μl, 100 mg protein/ml). The tubes were rotated again for an additional 16 hours at room temperature. The reaction mixtures were then centrifuged, the supernatants decanted, and the particles resuspended in phosphate buffered saline solution (1 ml, pH 7.4). This step was repeated four times, and during the last time, the solids were resuspended in phosphate buffered saline solution (1.8 ml) and merthiolate preservative (0.02%) was added.

Antibodies were attached to the Control particles by mixing the antibodies (0.3 mg) with a suspension of the particles (30 mg dry weight), in N-2-hydroxyethylpiperazine-N'-2-ethanesulfonic acid buffer (0.1 molar, pH 8.5, 1.5 ml). After end-over-end rotation for 24 hours at room temperature, the reactions were treated as described above.

The relative amounts of active antibody on the particles was determined by measuring the ability of the reagents to react with thyroxine labeled with either horseradish peroxidase or alkaline phosphatase. The horseradish peroxidase-labeled antigen was prepared using a procedure similar to that described by Kunst et al, *Clin. Chem.*, 34(9), pp. 1830–1833 (1988). The alkaline phosphatase-labeled antigen was prepared using a procedure similar to that described by Ito et al, *Clin. Chem.*, 30(10), pp. 1682–1685 (1984). This measurement was conducted as follows with the thyroxine-alkaline phosphatase analog being used at $10^{-9}$ molar and the thyroxine-peroxidase analog being used at $5 \times 10^{-11}$ molar:

The relative amounts of active antibody in the resulting dispersions were determined in an assay in which serial dilutions of the reagent dispersions were mixed with a fixed concentration of either the peroxidase-labeled analog or the alkaline phosphatase-labeled analog. The dilutions were incubated for about one hour with constant agitation at room temperature in phosphate buffered saline solution containing bovine serum albumin (1%). The amount of labeled analog remaining in solution after centrifugation was determined, and the concentration of thyroxine binding sites required to bind 50% of the labeled analog was calculated.

The following Table I shows the results of the active antibody measurements. The results indicate that with most of the antibodies tested, less reagent was required to bind the labeled analog using the reagents prepared according to this invention, as compared to the use of the Control reagents.

For example, with antibody D, 24 nmolar binding antibody binding sites are required to bind 50% of the alkaline phosphatase-labeled analog using the reagents prepared by this invention while 44 nmolar antibody binding sites are required to bind 50% of the same labeled analog using the Control reagent. This represents an 83% improvement with the present invention. Similarly, using the same antibody D and the horseradish peroxidase-labeled analog, use of the reagent prepared by the present invention provides a 188% improvement over the Control reagents.

TABLE I

| | Theoretical Thyroxine Binding Sites Where 50% of Label Binding is Achieved (nmmolar) | | | |
|---|---|---|---|---|
| | Thyroxine Alkaline Phosphatase Analog | | Thyroxine Peroxidase Analog | |
| Antibodies | Invention | Control | Invention | Control |
| A | 10 | 5.9 | 3.3 | 3.2 |
| B | 14 | 32 | 14 | 21 |

TABLE I-continued

| | Theoretical Thyroxine Binding Sites Where 50% of Label Binding is Achieved (nmmolar) | | | |
|---|---|---|---|---|
| | Thyroxine Alkaline Phosphatase Analog | | Thyroxine Peroxidase Analog | |
| Antibodies | Invention | Control | Invention | Control |
| C | 3.9 | 4.8 | 2.6 | 3.2 |
| D | 24 | 44 | 9.0 | 26 |
| E | 39 | 39 | 19 | 26 |
| F | 3.5 | 21 | 2.1 | 8.6 |
| G | 37 | 59 | 21 | 32 |
| H | 15 | 12 | 10 | 5.9 |
| I | 2.9 | 39 | 2.0 | 19 |
| J | 11 | 13 | 6.9 | 10 |
| K | 30 | 44 | 30 | 19 |

EXAMPLE 2

Preparation of Reagents Having Labeled Bovine Gamma Globulin

This example illustrates the practice of this invention to attach radio-labeled bovine gamma globulin to carboxylated polymeric particles.

Materials:

The carboxylated particles used were as follows:

Test A: Poly(styrene-co-mono-2-methacryloyloxyethyl glutarate) (97.84:2.16 molar ratio), Test B: Poly(styrene-co-mono-m- and p-vinylbenzyl glutarate) (97.8:2.2 molar ratio), Test C: Poly[styrene-co-monomethacryloylpenta(oxyethylene) glutarate] (98.7:1.3 molar ratio), and Test D: Poly(styrene-co-acrylic acid) (95:5 molar ratio).

The activating agents used were 1-(4-morpholinocarbonyl)-4-(2-sulfoethyl)pyridinium hydroxide, inner salt (Control, prepared by the procedures described in GB-A-1,383,630, that is the reaction of 4-morpholinocarbonyl chloride with 2-(4-pyridinoethanesulfonic acid), and 1-(1-pyrrolidinylcarbonyl)pyridinium chloride (Invention).

Method:

All polymers were treated under the same conditions. The final dispersions comprised 1% of $^3$H bovine gamma globulin per gram of polymeric particles (0.3 mg of protein per 30 mg dry polymer weight) in 2-(4-morpholino)ethanesulfonic acid buffer (0.1 molar, pH 5.5). The amount of activating agent used was either 16.6 mg of the hydroxide, inner salt, or 9.6 mg of the chloride.

The reaction dispersions were prepared by adding suspensions of the particles (30 mg dry weight each) to large microfuge tubes and each was brought to a volume of 1.5 ml using the buffer. The resulting suspensions were centrifuged for 15 minutes at 14,000 rpm and the supernatants discarded. Buffer (1 ml) was added to each tube, followed by addition of a solution of the activating agent (300 μl) to each tube. The solution of the hydroxide, inner salt (Control) was prepared by dissolving 199 mg in 3.6 ml of the buffer, and the solution of the chloride (Invention) was prepared by dissolving 115 mg in 3.6 ml of the buffer.

The tubes were then capped and rotated end-over-end at room temperature for 10 minutes. A solution (30 μl) of the labeled protein (10 mg/ml) was added to each tube followed by rotation end-over-end for 4 hours at room temperature.

Reaction of the protein with the carboxy activated carboxy groups on the particles was quenched by the addition of bovine serum albumin (250 μl, 100 mg protein/ml) to each tube. The tubes were then rotated again for an additional 16 hours at room temperature, and each reaction mixture (250 μl) was removed to determine the total labeled protein.

A sample (500 μl) of each reaction mixture was also removed and treated with buffer (400 μl, 0.1 molar) and a solution of sodium dodecyl sulfate (100 μl, 10% in deionized distilled water). The resulting mixtures were further mixed by tumbling at 37° C. for 16 hours on a rotating disc mounted at a 45° angle (the treatment with surfactant removed absorbed, but not covalently bound, protein from the particles). The reaction mixtures were centrifuged, and aliquots (500 μl) were removed to determine the amount of free labeled protein.

The total amount of $^3$H bovine gamma globulin bound to the particles, the amount of labeled protein covalently bound to the particles, and the covalent/total bound ratio are shown below in Table II. The data show that the method of this invention provides efficient covalent binding of bovine gamma globulin. While the Control method appears to be equivalent or better in some cases, the Control method is not desirable for other reasons, namely the activity of the proteins are not retained as readily on the particles when the Control activating agent is used (see for example, the results of Example 3 below), and the Control activating agent is not as stable for long-term storage.

TABLE II

| Activating Agent | Polymeric Particles | Total % Bound | Covalent % Bound | Ratio Covalent/Total |
|---|---|---|---|---|
| Control | Test A | 97 | 96 | 99 |
| Invention | Test A | 91 | 89 | 98 |
| Control | Test B | 97 | 97 | 100 |
| Invention | Test B | 94 | 93 | 99 |
| Control | Test C | 90 | 90 | 100 |
| Invention | Test C | 49 | 48 | 100 |
| Control | Test D | 97 | 97 | 100 |
| Invention | Test D | 95 | 94 | 99 |

EXAMPLE 3

Attachment of Anti-Thyroxine Antibodies to Various Carboxylated Particles

This example illustrates the preparation of reagents using the method of this invention and comparing the retention of activity of the protein (that is, antibody) to that using a method of the prior art.

The procedure described in Example 2 above was used to attach monoclonal antibodies directed to thyroxine (available from Cambridge/Ventrex Laboratories, Inc.) to various carboxylated particles (Tests A-D shown in Example 2 above). The antibodies were used in solution (130 μl, 2.3 mg protein/ml). The activating agents used were
1-(4-morpholinocarbonyl)-4-(2-sulfoethyl)pyridinium hydroxide, inner salt (Control), and
1-(1-pyrrolidinylcarbonyl)pyridinium chloride (Invention).

The reaction was quenched, the reaction mixtures were centrifuged, the supernatants decanted, and the resulting reagents resuspended in phosphate buffered saline solution (1 ml, pH 7.4). This step was repeated four times, and during the last time, the solids were resuspended in phosphate buffered saline solution (1.8 ml) and merthiolate preservative (0.02%) was added.

The relative amounts of active antibody in the resulting dispersions were determined in an assay in which serial dilutions of the reagent dispersions were mixed with a fixed concentration of alkaline phosphatase-labeled thyroxine (prepared as described in Example 1 above). The dilutions were incubated for about one hour with constant agitation at room temperature in phosphate buffered saline solution containing bovine serum albumin (1%). The amount of labeled analog remaining in solution after centrifugation was determined, and the concentration of thyroxine binding sites required to bind 50% of the labeled analog was calculated. The results are summarized in Table II below. They show that the method of this invention using 1-(1-pyrrolidinylcarbonyl)pyridinium chloride activating agent provided reagents which retained antibody activity better than the reagents prepared using the Control method. For each polymer, the Control method required about twice the amount of reagent to bind 50% of the labeled thyroxine as compared to the method of this invention.

TABLE III

| Polymeric Particles | Theoretical Thyroxine Binding Sites Where 50% of Analog is Bound (nmolar) | |
|---|---|---|
| | Control | Invention |
| Test A | 20 | 10 |
| Test B | 23 | 13 |
| Test C | 36 | 16 |
| Test D | 100 | 56 |

EXAMPLE 4

Comparison of Reagents Prepared Using Different Activating Agents and Two Preparatory Procedures This example illustrates the covalent attachment of radio-labeled protein with carboxylated particles using several activating agents described herein and two different preparatory procedures.

Materials:

The particles used were composed of poly[styrene-co-mono-2-(p-vinylbenzylthio)ethyl glutarate] (98.25:1.75 molar ratio).

The activating agents were Compounds I, VIII and IV described above. Two Control activating agents used were (A) 1-(4-morpholinocarbonyl)-4-(2-sulfoethyl)pyridinium hydroxide, inner salt, and (B) N-(3-N,N-dimethylaminopropyl)-N'-ethylcarbodiimide hydrochloride.

The attached protein was $^3$H bovine gamma globulin.

Preparatory Methods:

The final dispersions comprised 1% of $^3$H bovine gamma globulin per gram of particles (0.3 mg protein/30 mg dry polymer weight). The amount of activating agent used was 1.5 mmole/g polymer or 45 μmoles/30 mg dry polymer weight.

In Method A, the reaction dispersions were prepared by adding suspensions of the particles (30 mg, 192 μl at 15.6% solids) to large microfuge tubes and each was brought to a volume of 1.5 ml with 2-(4-morpholino)ethanesulfonic acid buffer (0.1 molar, pH 5.5). The resulting suspensions were centrifuged for 15 minutes at 14,000 rpm and the supernatants discarded. Buffer (1 ml) was added to each tube, followed by addition of a solution of the activating agent (300 μl) to each tube. The activating agent solutions (0.15 molar) were prepared in buffer. The tubes were then capped and rotated end-over-end at room temperature for 10 minutes. A solution (30 μl) of the labeled protein (10 mg/ml) was added to each tube followed by rotation end-over-end for 24 hours at room temperature.

In Method B, the reaction dispersions were prepared as described above, but after the 10-minute activation step, the activated particles were centrifuged, the supernatant was removed and the particles were resuspended in phosphate buffered saline solution (1.3 ml). A solution (30 μl) of labeled protein (10 mg/ml) was added to each tube, followed by rotation end-over-end for 24 hours at room temperature. Thus, in this method, excess activating agent was removed before protein was attached to the activated particles.

All reactions were quenched and assayed for the total amount of labeled protein bound as well as the amount of protein which was covalently bound according to the procedures described in Example 2 above.

The results are shown below in Table IV. These data indicate that all activating agents provide high total and covalent binding of the protein when Method A is followed (no removal of excess activating agent). However, Compound I provides the best binding of protein of the carbamoylonium compounds when excess activating agent is removed (Method B). Method B might be used when proteins are unstable at low pH (5.5), or when the proteins are sensitive to the presence of activating agent.

As noted above, Control A activating agent, while it provides high protein binding, is undesirable because it produces undesired by-products which prematurely terminate the attachment of protein. Moreover, the carbodiimide of Control B is not desirable because it promotes protein crosslinking and reduces the retention of antibody activity. Thus, Compounds I, IV and VIII provide advantages in the practice of this invention and Compound I is most preferred.

TABLE IV

| Activating Agent | Method | Total % Bound | % Covalent Bound | Binding Total Covalent:Total |
|---|---|---|---|---|
| I | A | 97 | 96 | 1.0 |
| I | B | 92 | 76 | 0.83 |
| VIII | A | 96 | 95 | 1.0 |
| VIII | B | 88 | 60 | 0.69 |
| IV | A | 82 | 76 | 0.93 |
| IV | B | 88 | 60 | 0.68 |
| Control A | A | 97 | 97 | 1.0 |
| Control A | B | 87 | 57 | 0.68 |
| Control B | A | 97 | 96 | 0.99 |
| Control B | B | 94 | 83 | 0.88 |

The invention has been described in detail with particular reference to preferred embodiments thereof, but it will be understood that variations and modifications can be effected within the spirit and scope of the invention. Moreover, all patents, patent applications (published or unpublished, foreign or domestic), literature references or other publications noted above are incorporated herein by reference for any disclosure pertinent to the practice of this invention.

We claim:

1. A method for attaching a reactive amine- or sulfhydryl-containing compound to polymeric particles comprising:

A. contacting (1) an aqueous suspension of carboxylated polymeric particles with (2) a 1-(1-pyrrolidinylcarbonyl)pyridinium salt to produce reactive intermediate polymer particles having intermediate reactive groups, and B. contacting the reactive intermediate polymer particles produced in step A with a compound having a reactive amine or sulfhydryl group which reacts with said intermediate reactive groups to form a covalent linkage between said particles and said reactive compound.

2. The method of claim 1 wherein either said polymeric particles used in step A or said reactive amine- or sulfhydryl-containing compound used in step B has a detectable tracer associated therewith.

3. The method of claim 1 wherein said reactive amine- or sulfhydryl-containing compound is selected from the groups consisting of amines, enzymes, amino acids, peptides, polypeptides, proteins, lipoproteins, glycoproteins, hormones, drugs, steroids, vitamins, polysaccharides, glycolipids, alkaloids, microorganisms, viruses, protozoa, fungi, parasites, rickettsia, molds, blood components, tissue and organ components, pharmaceuticals, haptens, lectins, toxins, nucleic acids, antigenic materials, biotin or derivatives thereof and components thereof.

4. The method of claim 3 wherein said compound is an antibody or antigenic material.

5. The method of claim 4 wherein said compound is an antibody directed to human chorionic gonadotropin, thyroxine, phenobarbital, phenytoin, digoxin, triiodothyronine, carbamazepine or theophylline.

6. The method of claim 1 wherein said pyridinium salt is present in a molar ratio to said carboxy groups of from about 1:1 to about 200:1.

7. The method of claim 1 wherein the weight ratio of said reactive amine- or sulfhydryl-containing compound to said polymeric particles is from about 1:2000 to about 1:2.

8. The method of claim 1 carried out at a temperature of from about 10° C. to about 60° C.

9. The method of claim 1 wherein said salt is represented by the structure:

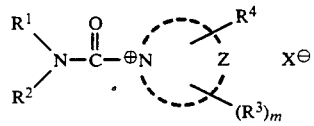

wherein

Z represents the carbon atoms necessary to complete a pyridinium ring, m is 0 or 1, $R^1$ and $R^2$ together represent the carbon atoms necessary to complete, with the nitrogen atom to which they are attached, a pyrrolidinyl ring, $R^3$ is alkyl, cycloalkyl, aryl, or a 5- to 7-membered heterocyclic group, or $R^3$ and $R^4$, taken together, can represent the carbon atoms necessary to complete, with the pyridinium ring, a fused 5- to 7-membered carbocyclic or heterocyclic ring, $R^4$ is hydrogen or alkyl, or when m is 0, $R^4$ can be any of:

(a) —$NR^5CO$—$R^6$ wherein $R^5$ is hydrogen or alkyl, and $R^6$ is hydrogen, alkyl as defined for $R^5$, or —$NR^7R^8$ wherein $R^7$ and $R^8$ are independently hydrogen or alkyl as defined for $R^5$, (b) —$(CH_2)_n$—$NR^9R^{10}$ wherein $R^9$ is —$COR^{11}$, $R^{10}$ is hydrogen or alkyl as defined for $R^5$, $R^{11}$ is hydrogen, alkyl as defined for $R^5$ or —$NR^{12}R^{13}$ wherein $R^{12}$ is alkyl as defined for $R^5$ or aryl, and $R^{13}$ is hydrogen, alkyl or aryl as defined for $R^{12}$, and n is 1 to 3, and (c) —$(CH_2)_q$—$CONR^{14}R^{15}$ wherein $R^{14}$ is hydrogen, alkyl or aryl as defined for $R^{12}$, $R^{15}$ is hydrogen or alkyl as defined for $R^5$, or $R^{14}$ and $R^{15}$ together represent the atoms necessary to complete a 5- to 7-membered aliphatic ring, and q is 0 to 3, and X⁻ represents an anion or an anionic portion of said salt to form an intramolecular salt.

10. The method of claim 9 wherein m is 0 and $R^4$ is hydrogen, alkyl, aryl, pyridinyl, or when m is 1, $R^3$ and $R^4$ together represent the carbon atoms necessary to complete a 6-membered fused carbocyclic ring.

11. The method of claim 9 wherein X⁻ is halide, tetrafluoroborate, nitrate, sulfate, p-toluenesulfonate, perchlorate, methosulfate, hydroxide or hexafluorophosphate, or is a sulfonate or an alkylenesulfonate attached to the pyridinium ring, wherein the alkylene portion has from 1 to 6 carbon atoms.

12. The method of claim 1 wherein said salt is selected from the group consisting of:

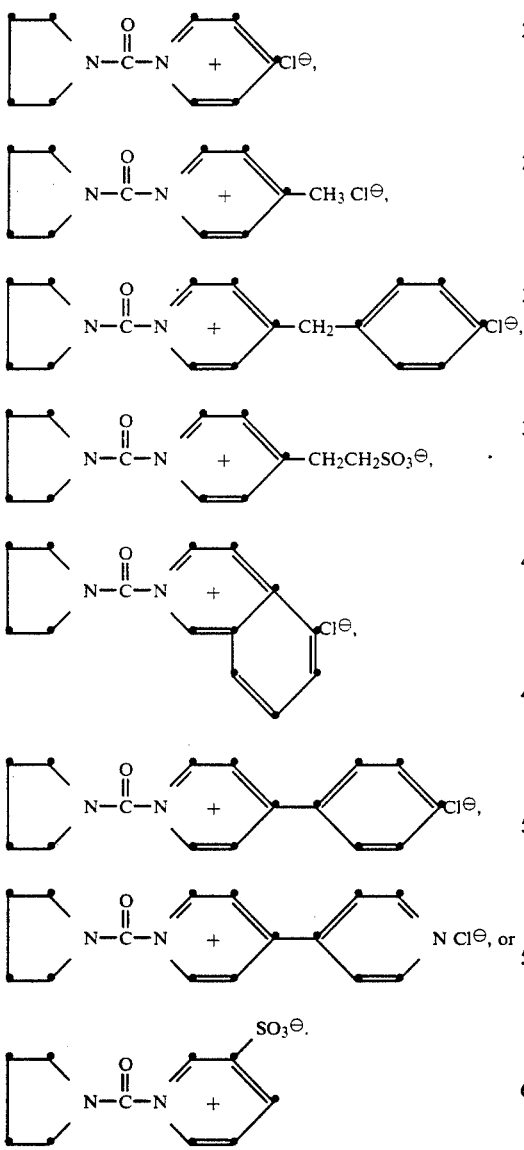

13. The method of claim 1 carried out using 1-(1-pyrrolidinylcarbonyl)pyridinium chloride.

14. The method of claim 1 wherein said carboxylated polymeric particles are composed of a polymer represented by the structure:

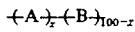

wherein A represents recurring units derived from one or more ethylenically unsaturated polymerizable monomers containing carboxyl groups or salts thereof or precursors of said groups, and B represents recurring units derived from one or more ethylenically unsaturated polymerizable monomers, and x is from about 0.1 to about 70 mole percent.

15. The method of claim 1 wherein B is derived from styrene or a styrene derivative, an acrylic or methacrylic acid ester, or acrylonitrile, and x is from about 1 to about 20 mole percent.

16. The method of claim 14 wherein A is derived from acrylic acid, methacrylic acid, itaconic acid, β-carboxyethyl acrylate, β-carboxyethyl methacrylate, m and p-carboxymethylstyrene, methacrylamidohexanoic acid or N-(2-carboxy-1,1-dimethylethyl)acrylamide, or a salt or anhydride precursor thereof.

17. The method of claim 14 wherein A is derived from an ethylenically unsaturated polymerizable monomer represented by the structure:

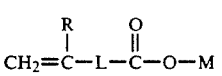

wherein R is hydrogen, halo or alkyl of 1 to 3 carbon atoms, M is hydrogen, an alkali metal ion or an ammonium ion and L is an organic linking group having from 8 to 50 atoms selected from the group consisting of carbon, nitrogen, oxygen and sulfur atoms in the linking chain.

18. The method of claim 17 wherein R is hydrogen or methyl, M is hydrogen or an alkali metal ion, and L comprises two or more alkylene or arylenealkylene groups which are connected or terminated with an oxy, thio, imino (—$NR^1$—), carbonyloxy (—COO—), carbonylimino (—$CONR^1$—), ureylene (—$NR^1CONR^1$—) or sulfonylimino (—$SO_2NR^1$—) group, wherein each $R^1$ is independently hydrogen, alkyl having 1 to 10 carbon atoms, cycloalkyl having 4 to 10 carbon atoms or aryl having 6 to 14 carbon atoms.

19. The method of claim 18 wherein L is p-phenylenemethyleneoxycarbonyltrimethylene, carbonyloxyethyleneoxycarbonyltrimethylene, carbonyloxyethyleneurylenepentamethylene, carbonylpenta(oxyethylene)oxycarbonyltrimethylene, carbonyldeca(oxyethylene)oxycarbonyltrimethylene, p-phenylenemethylenethioethyleneoxycarbonyltrimethylene, carbonyloxyethyleneiminocarbonyltrimethylene, carbonyloxytetramethyleneoxycarbonyltetramethylene, p-phenylenemethyleneiminocarbonyltrimethylene, p-phenylenemethyleneiminocarbonyltrimethylene, p-phenylene(methyl)iminoethyleneoxycarbonyltri-methylene, p-phenylenemethylenethioethylene, p-phenylenemethylenethioethyleneiminocarbonylmethylene-oxymethylene, p-phenylenemethylenethioethyleneimino-carbonylmethylenethiomethylene, p-phenylene-methylenethioethyleneiminocarbonyltrimethylene, phenylenemethylenethio-1-carboxyethylene, phenylenemethylenethiophenylene, phenylenemethylenethioethyleneoxyethylenethiomethyleneoxycarbonylethylene, phenylenemethyleneoxyphenylenemethylene-thioethylene, phenylenemethylenethioethyleneoxy-ethylenethioethyleneoxycarbonylethylene, phenylene-methyleneoxyphenylenemethylenethiophenylenemethylene-thiotrimethylene and phenylenemethylenethioethylene-oxyethylenethioethyleneoxycarbonylphenylene.

20. The method of claim 14 wherein A is derived from the group consisting of: mono-m and p-vinylbenzyl glutarate, mono-p-vinylbenzyl glutarate, mono-2-methacryloyloxyethyl glutarate, 2-(4-carboxybutyramido)ethyl methacrylate, 2-[N'-(5-carboxypentyl)ureido]ethyl methacrylate, mono-methacryloylpenta(oxyethylene) glutarate, mono-(4-acryloyloxybutyl) glutarate, 4-(4-carboxybutyramido)styrene, mono-methacryloyldeca(oxyethylene) glutarate, mono-2-(p-vinylbenzylthio)ethyl glutarate, mono-2-(m and p-vinylbenzylthio)ethyl glutarate, 4-(4-carboxybutyramidomethyl)styrene, mono-2-[N-methyl-N-(4-vinylbenzyl)amino]ethyl glutarate, 3-(p-vinylbenzlthio)propionic acid, 4-[2-(4-carboxybutyramido)ethylthiomethyl]styrene, 4-[2-(carboxymethoxyacetamido)ethylthiomethyl]styrene, 4-[2-(carboxymethylthioacetamido)ethylthiomethyl]styrene, mono-2-(4-vinylbenzylthio)ethyl succinate, 4-[2-(carboxymethoxyacetoxy)ethylthiomethyl]styrene, mono-4-vinylbenzyl succinate, 2-(4-vinylbenzylthio)succinic acid, 2-(4-vinylbenzylthio)benzoic acid, mono-2-[2-(4-vinylbenzylthio)ethoxy]ethylthiomethyl malonate, mono-methacryloylpenta(oxyethylene) phthlate, mono-methacryloyldeca(oxyethylene) phthalate, mono-2-{2-[2-(4-vinylbenzylthio)ethoxy]ethylthio}ethyl succinate, mono-2-{2-[2-(4-vinylbenzylthio)ethoxy]ethylthio}ethyl phthalate, 3-[4-(4-vinylbenzyloxy)benzylthio]propionic acid and 4-{4-[4-(4-vinylbenzyloxy)benzylthio]benzylthio}butyric acid.

21. The method of claim 1 wherein said polymeric particles are core-shell particles wherein the core is composed of a first polymer and the shell is composed of a carboxylated second polymer.

22. A kit comprising:
a. polymeric particles having reactive carboxyl groups, or salts or precursors thereof, on the surface thereof, and
b. a 1-(1-pyrrolidinylcarbonyl)pyridinium salt.

23. The kit of claim 22 wherein said particles have a detectable tracer associated therewith.

24. The kit of claim 23 wherein said detectable tracer is a colorimetric or fluorometric dye incorporated within the particles.

25. The kit of claim 22 wherein said polymeric particles are composed of a carboxylated polymer represented by the structure:

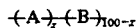

wherein A represents recurring units derived from one or more ethylenically unsaturated polymerizable monomers containing carboxyl groups or salts thereof or precursors of said groups, and B represents recurring units derived from one or more ethylenically unsaturated polymerizable monomers, and x is from about 0.1 to about 70 mole percent.

26. The kit of claim 22 wherein said polymeric particles are provided in an aqueous suspension.

27. The kit of claim 22 comprising 1-(1-pyrrolidinylcarbonyl)pyridinium chloride.

* * * * *